US011524293B2

(12) United States Patent
Patel et al.

(10) Patent No.: US 11,524,293 B2
(45) Date of Patent: Dec. 13, 2022

(54) CELL SEPARATION DEVICE, METHOD AND SYSTEM

(71) Applicant: Sartorius Stedim North America Inc., Bohemia, NY (US)

(72) Inventors: Grishma Patel, Northville, MI (US); Mark S. Szczypka, Ann Arbor, MI (US); David Splan, Brighton, MI (US)

(73) Assignee: Sartorius Stedim North America Inc., Bohemia, NY (US)

( * ) Notice: Subject to any disclaimer, the term of this patent is extended or adjusted under 35 U.S.C. 154(b) by 1297 days.

(21) Appl. No.: 15/873,039

(22) Filed: Jan. 17, 2018

(65) Prior Publication Data

US 2019/0217296 A1   Jul. 18, 2019

(51) Int. Cl.
| | |
|---|---|
| *B01L 3/00* | (2006.01) |
| *C12N 1/02* | (2006.01) |
| *G01N 33/49* | (2006.01) |
| *C12M 1/00* | (2006.01) |
| *C12M 3/00* | (2006.01) |
| *C12M 1/12* | (2006.01) |

(52) U.S. Cl.
CPC ......... *B01L 3/502761* (2013.01); *B01L 3/502* (2013.01); *B01L 3/50273* (2013.01); *B01L 3/502746* (2013.01); *B01L 3/502753* (2013.01); *C12M 3/00* (2013.01); *C12M 23/14* (2013.01); *C12M 25/14* (2013.01); *C12M 47/02* (2013.01); *C12N 1/02* (2013.01); *G01N 33/491* (2013.01); *B01L 2200/028* (2013.01); *B01L 2200/0636* (2013.01); *B01L 2200/0652* (2013.01); *B01L 2200/0668* (2013.01); *B01L 2300/0681* (2013.01); *B01L 2300/0864* (2013.01); *B01L 2400/08* (2013.01)

(58) Field of Classification Search
CPC ....... B01L 2200/028; B01L 2200/0636; B01L 2200/0652; B01L 2200/0668; B01L 2300/0681; B01L 2300/0864; B01L 2400/08; B01L 3/502; B01L 3/50273; B01L 3/502746; B01L 3/502753; B01L 3/502761; C12M 23/14; C12M 25/14; C12M 3/00; C12M 47/02; C12N 1/02; G01N 33/491

See application file for complete search history.

(56) References Cited

U.S. PATENT DOCUMENTS

| | | | |
|---|---|---|---|
| 8,679,751 B2 * | 3/2014 | Huang | B01L 3/502753 435/34 |
| 8,934,700 B2 * | 1/2015 | Bharadwaj | C12N 5/0087 382/133 |
| 9,376,655 B2 | 6/2016 | Larsen et al. | |
| 10,301,585 B2 | 5/2019 | Larsen et al. | |
| 10,934,514 B2 | 3/2021 | Larsen et al. | |
| 2011/0065181 A1 | 3/2011 | Hvichia | |
| 2012/0238011 A1 | 9/2012 | Tuohey et al. | |
| 2013/0337500 A1 * | 12/2013 | Tan | G01N 33/57407 435/308.1 |
| 2014/0072953 A1 | 3/2014 | Hvichia | |
| 2015/0368619 A1 | 12/2015 | Kim et al. | |
| 2017/0252705 A1 | 9/2017 | Dibiasio et al. | |
| 2021/0179995 A1 | 6/2021 | Larsen et al. | |

FOREIGN PATENT DOCUMENTS

WO   WO 2012/139209 A1   10/2012

* cited by examiner

*Primary Examiner* — Blaine Lankford
(74) *Attorney, Agent, or Firm* — Klarquist Sparkman, LLP

(57) ABSTRACT

Cell separation systems, and methods for separating cells from microcarriers, and harvesting the separated cells, are provided, wherein the system comprises a cell separation device, a cell settling device, and a cell screening device.

8 Claims, 9 Drawing Sheets

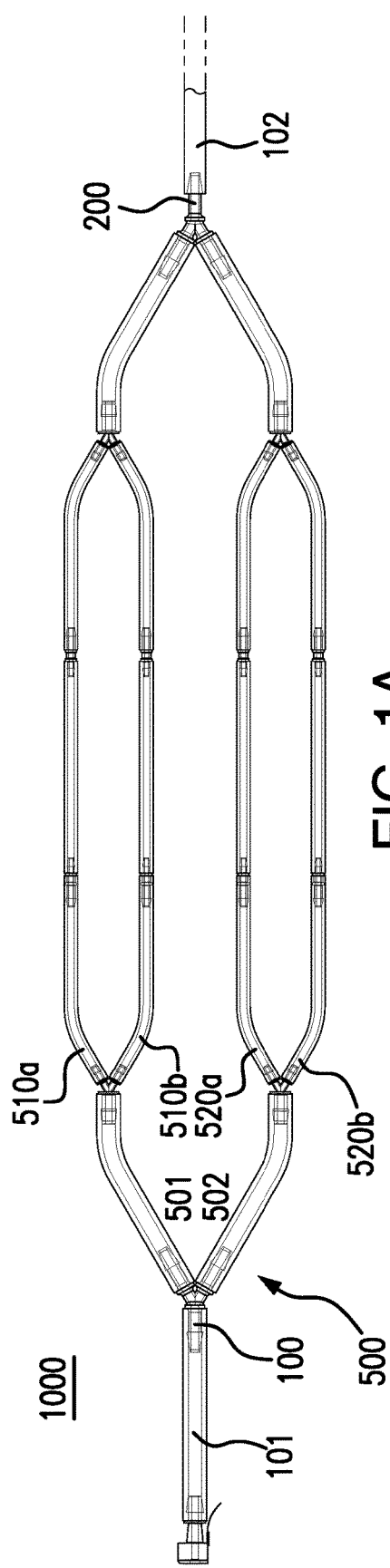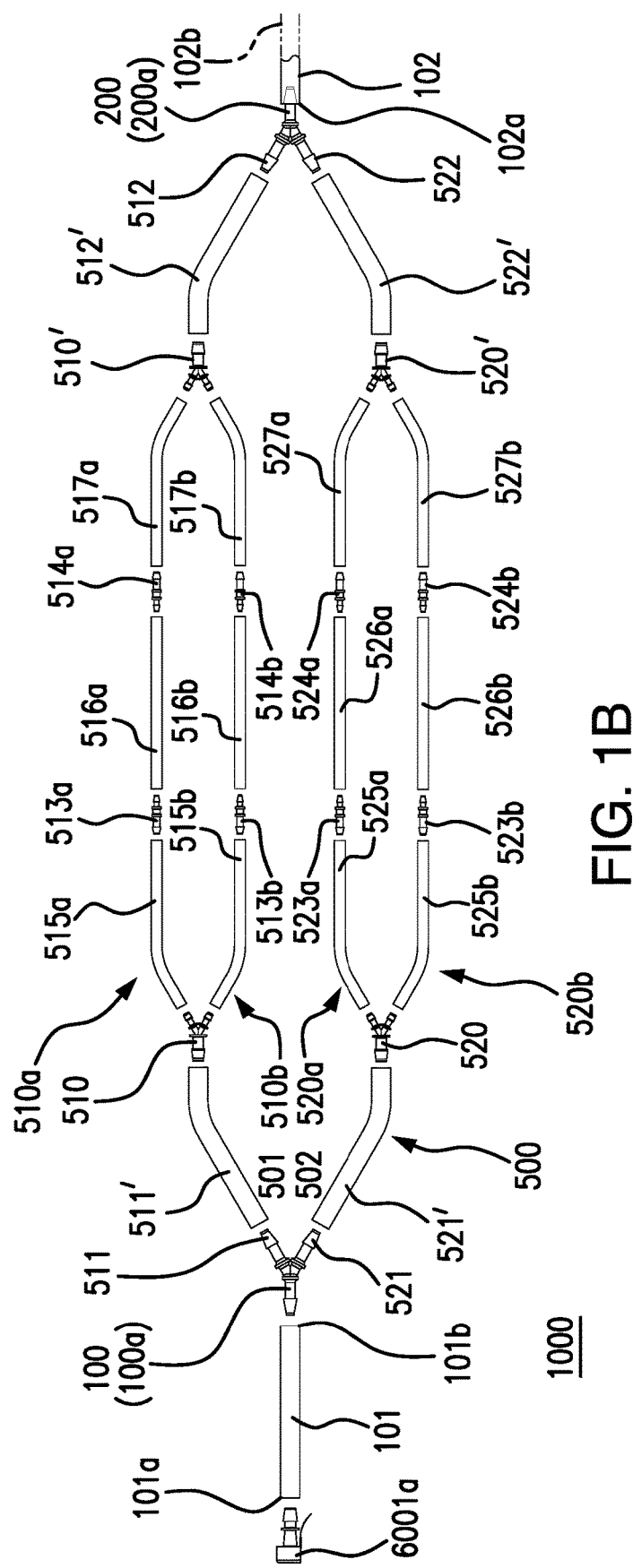
FIG. 1A
FIG. 1B

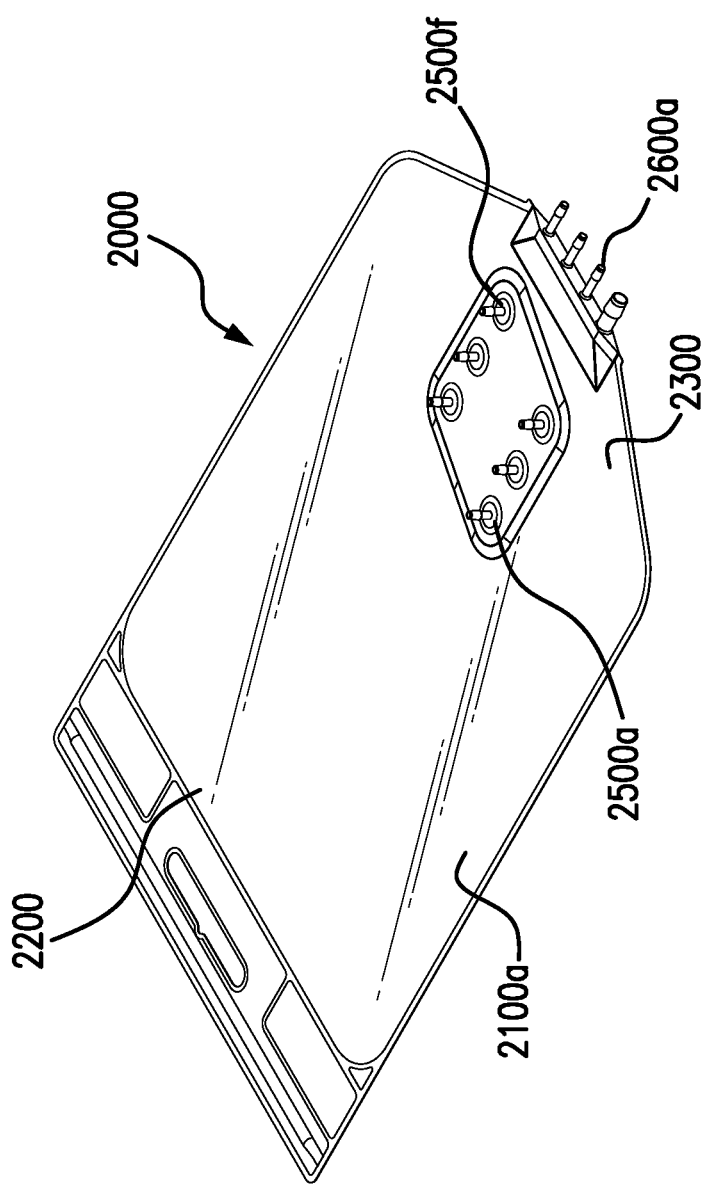

CELL SEPARATION DEVICE, METHOD AND SYSTEM

BACKGROUND OF THE INVENTION

Cells can be cultured for a variety of uses, for example, to manufacture biological products and pharmaceutical products. Some cells are cultured while attached to microcarriers such as beads, and the cells are separated from the microcarriers and subsequently harvested for further use.

However, there is a need for improved devices, methods, and systems for separating cells from microcarriers, and for providing suspensions of single cells. The present invention provides for ameliorating at least some of the disadvantages of the prior art. These and other advantages of the present invention will be apparent from the description as set forth below.

BRIEF SUMMARY OF THE INVENTION

An embodiment of the invention provides a cell separation system comprising A) a conduit for fluid communication with a source container, the source container comprising a fluid comprising cells, the conduit having a first end and a second end; B) a cell separation device comprising (a) an inlet having an inlet inner diameter, and an outlet having an outlet inner diameter, wherein the inlet is in fluid communication with the second end of the conduit for fluid communication with the source container; (b) a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter; C) a cell settling device comprising (a) a flexible bag having an interior volume, the flexible bag comprising at least two opposing side walls, each side wall having an interior surface and an exterior surface; a top end; a bottom end; and (b) a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least one port arranged at the bottom end of the bag, wherein the at least one port arranged at the bottom end of the bag is in fluid communication with the outlet of the cell separation device; and, D) a cell screening device comprising at least one inlet port and at least one outlet port, an interior volume, and a porous element between the at least one inlet port and the at least one outlet port, the ports allowing fluid to pass into and/or out of the cell screening device, wherein the cell screening device is arranged to allow fluid comprising cells and microcarriers to pass through the inlet port into the interior volume of the cell screening device, the cells passing through the porous element and through the outlet port, the microcarriers being retained by the porous element.

In another embodiment, a cell separation device comprises (a) an inlet having an inlet inner diameter, and an outlet having an outlet inner diameter; (b) a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths comprising a plurality of conduits fluidly connected by one or more connectors, each connector having at least one internal diameter, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths comprising a plurality of conduits fluidly connected by one or more connectors, each connector having at least one internal diameter, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter.

In yet another embodiment, a cell settling device comprises (a) a flexible bag having an interior volume, the flexible bag comprising at least two opposing side walls, each side wall having an interior surface and an exterior surface; a top end; a bottom end; and (b) a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least one port arranged at the bottom end of the bag.

In an additional embodiment, a cell screening device comprises at least one inlet port and at least one outlet port, an interior volume, and a porous element between the at least one inlet port and the at least one outlet port, the ports allowing fluid to pass into and/or out of the cell screening device, wherein the cell screening device is arranged to allow fluid comprising cells and microcarriers to pass through the inlet port into the interior volume of the cell screening device, the cells passing through the porous element and through the outlet port, the microcarriers being retained by the porous element.

Illustratively, in one embodiment, the cell screening device comprises (a) a flexible bag having an interior volume, the flexible bag comprising at least two opposing side walls, each side wall having an interior surface and an exterior surface; a top end; a bottom end; and (b) a porous element comprising a screen having a nominal mesh size of at least about 30 micrometers arranged in the interior volume of the flexible bag, the screen forming a pouch having an open end and a closed end; (c) a plurality of ports in fluid communication with the interior volume of the flexible bag, the ports allowing fluid to pass into and/or out of the bag, the plurality of ports including at least one inlet port arranged in one of the opposing side walls and passing through the side wall, and at least one outlet port arranged at the bottom end of the bag; wherein the cell screening device is arranged to allow fluid comprising cells and microcarriers to pass through the inlet port into the interior volume of the bag, the cells passing through the open end and closed end of the screen pouch and through the outlet port, the microcarriers being retained at the closed end of the screen pouch.

In another illustrative embodiment, the cell screening device comprises (a) a housing having an interior volume; and a (b) porous element arranged in the interior volume of the housing, the porous element having a pore structure allowing fluid comprising cells to pass therethrough, but preventing the passage of microcarriers therethrough; (c) a plurality of ports in fluid communication with the interior volume of the housing, the ports allowing fluid to pass into and/or out of the housing, the plurality of ports including at least one inlet port, and at least one outlet port arranged at the bottom end of the housing; wherein the cell screening device is arranged to allow fluid comprising cells and microcarriers to pass through the inlet port into the interior volume of the housing, the cells passing through the porous element and through the outlet port, the microcarriers being retained by the porous element.

In accordance with embodiments of methods according to the invention, a method of separating cells from microcarriers comprises passing a fluid comprising cells attached to microcarriers through an embodiment of the cell separation device; and a method of separating cells from microcarrriers and harvesting the separated cells comprises passing a fluid comprising cells attached to microcarriers through an embodiment of the cell separation system.

BRIEF DESCRIPTION OF THE SEVERAL VIEWS OF THE DRAWING(S)

FIGS. 1A and 1B show an embodiment of a cell separation device according to the present invention, wherein FIG. 1A shows an assembled view, and FIG. 1B shows an exploded view.

FIG. 2B is a perspective view of the cell settling device shown in FIG. 2A.

Figure 3A:
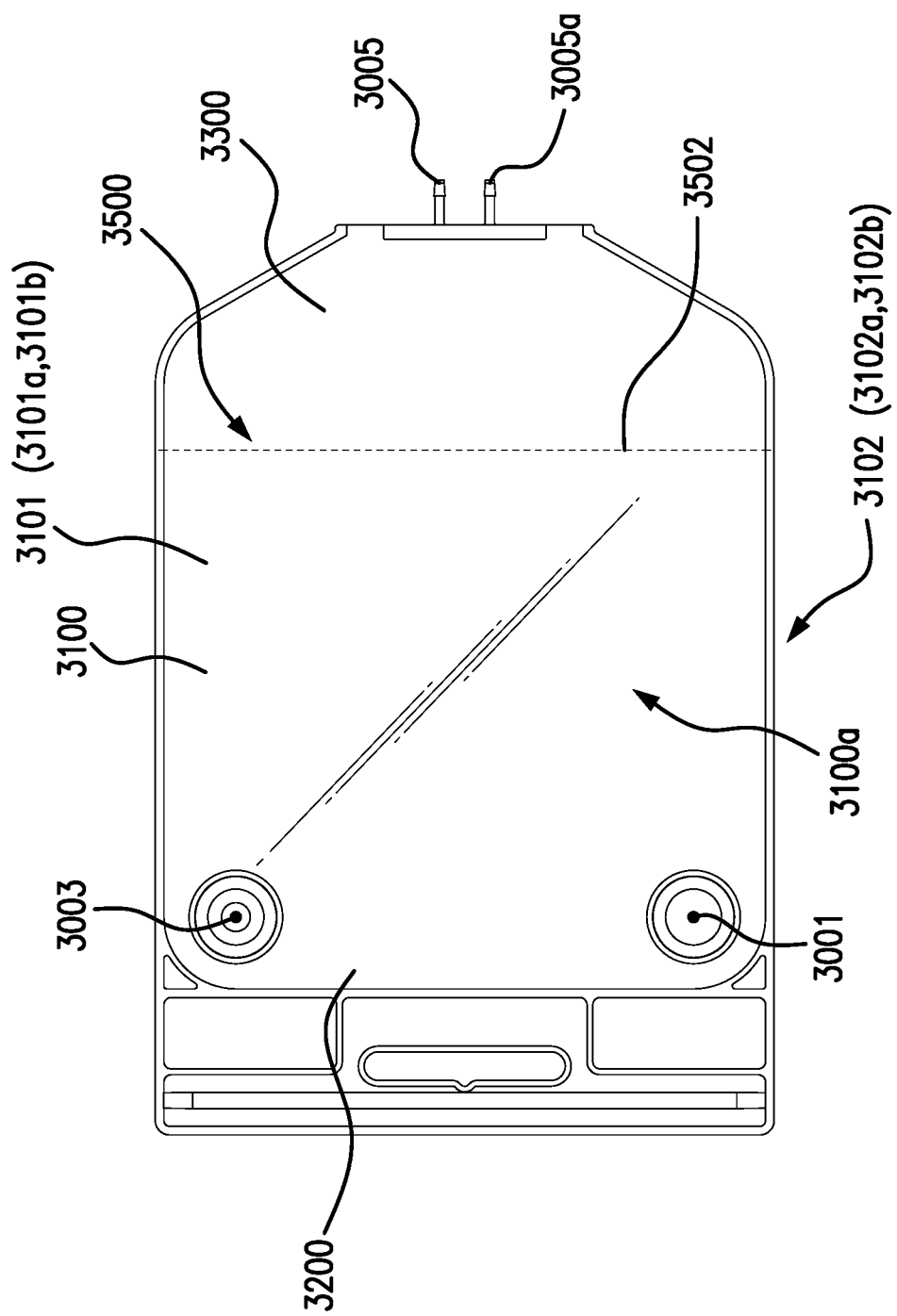
Figure 3B:
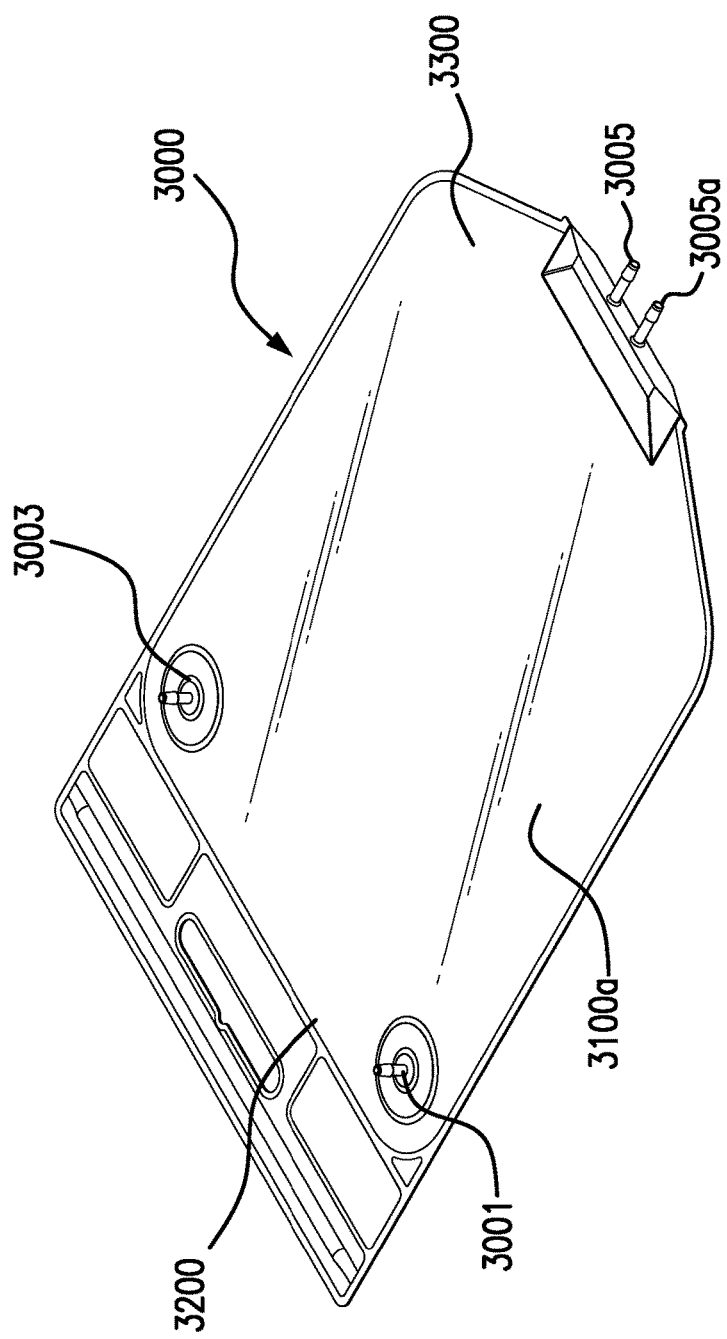

FIG. 3A is a top view of an embodiment of an embodiment of a cell screening device (or cell/microcarrier separation device) according to an embodiment of the present invention. FIG. 3B is a perspective view of the cell screening device shown in FIG. 3A, and FIG. 3C is a partial longitudinal cross-sectional view of the cell screening device shown in FIG. 3A, also showing the closed end of the screen pouch.

Figure 3C:
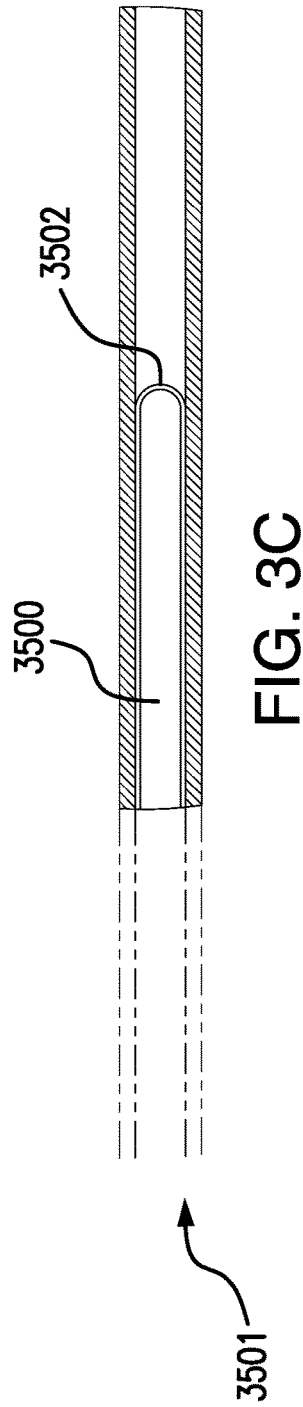
Figure 3D:
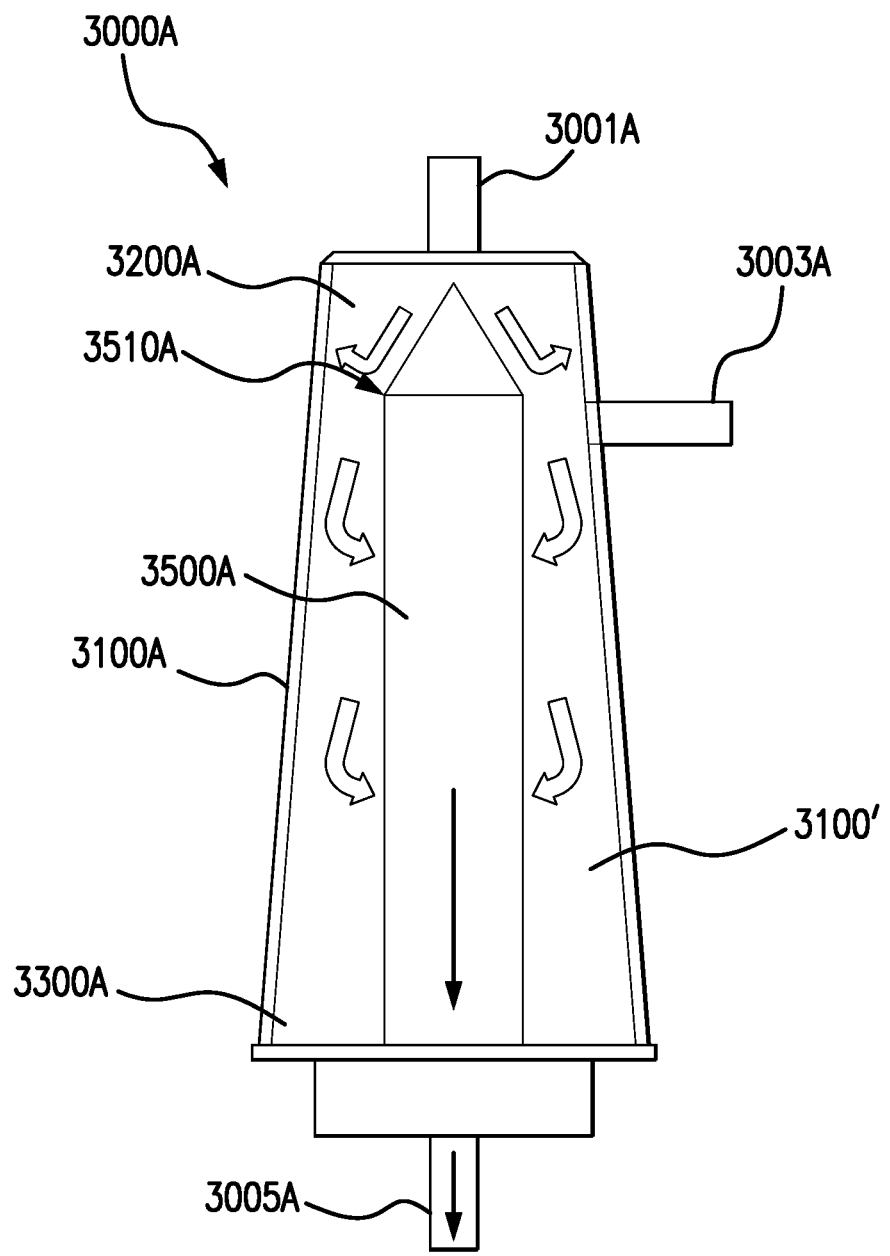

FIG. 3D is a diagrammatic view of another embodiment of a cell screening device (or cell/microcarrier separation device) according to an embodiment of the present invention.

Figure 4:
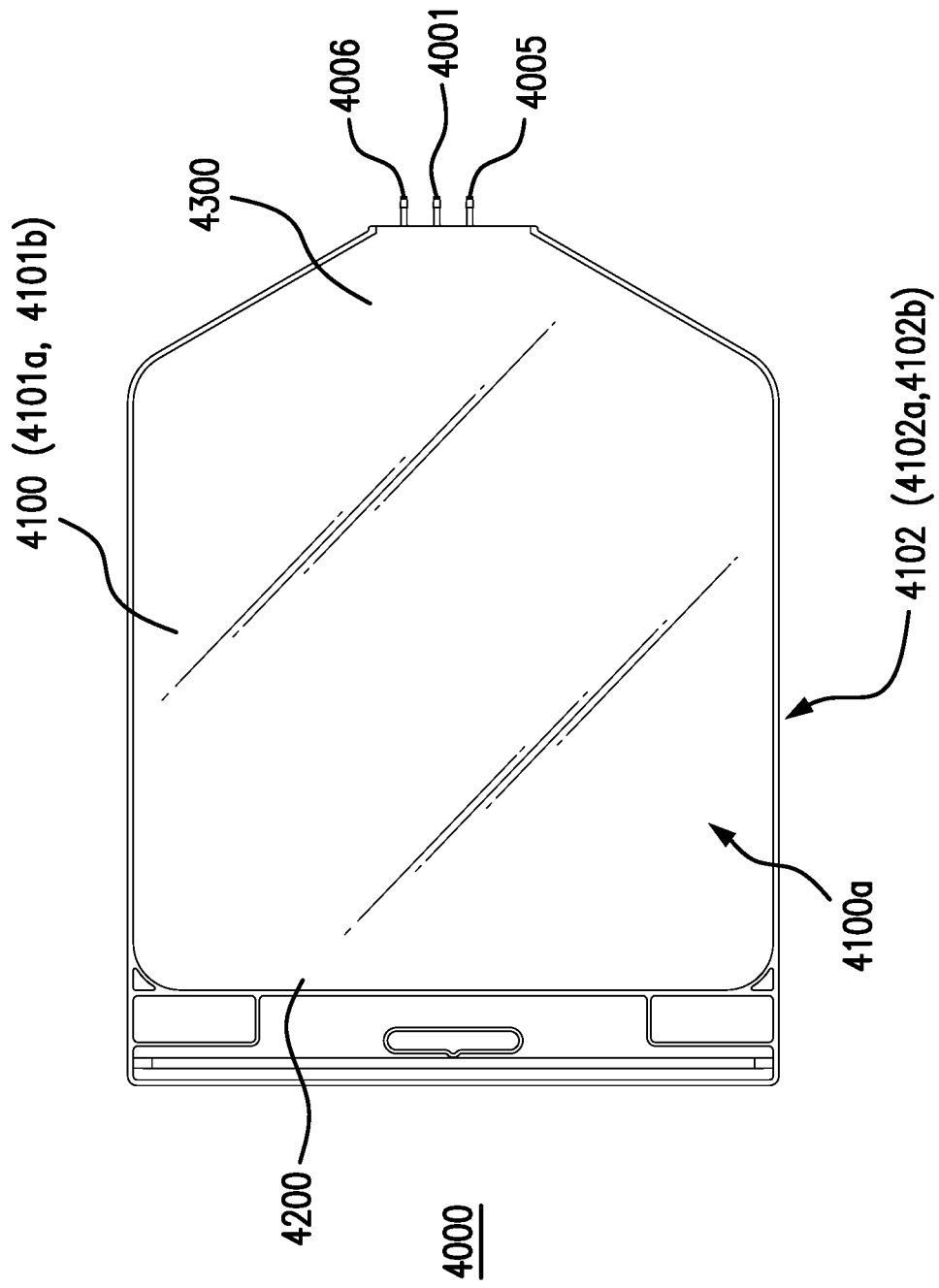

FIG. 4 is a top view of an embodiment of a harvest container of the present invention.

Figure 5A:
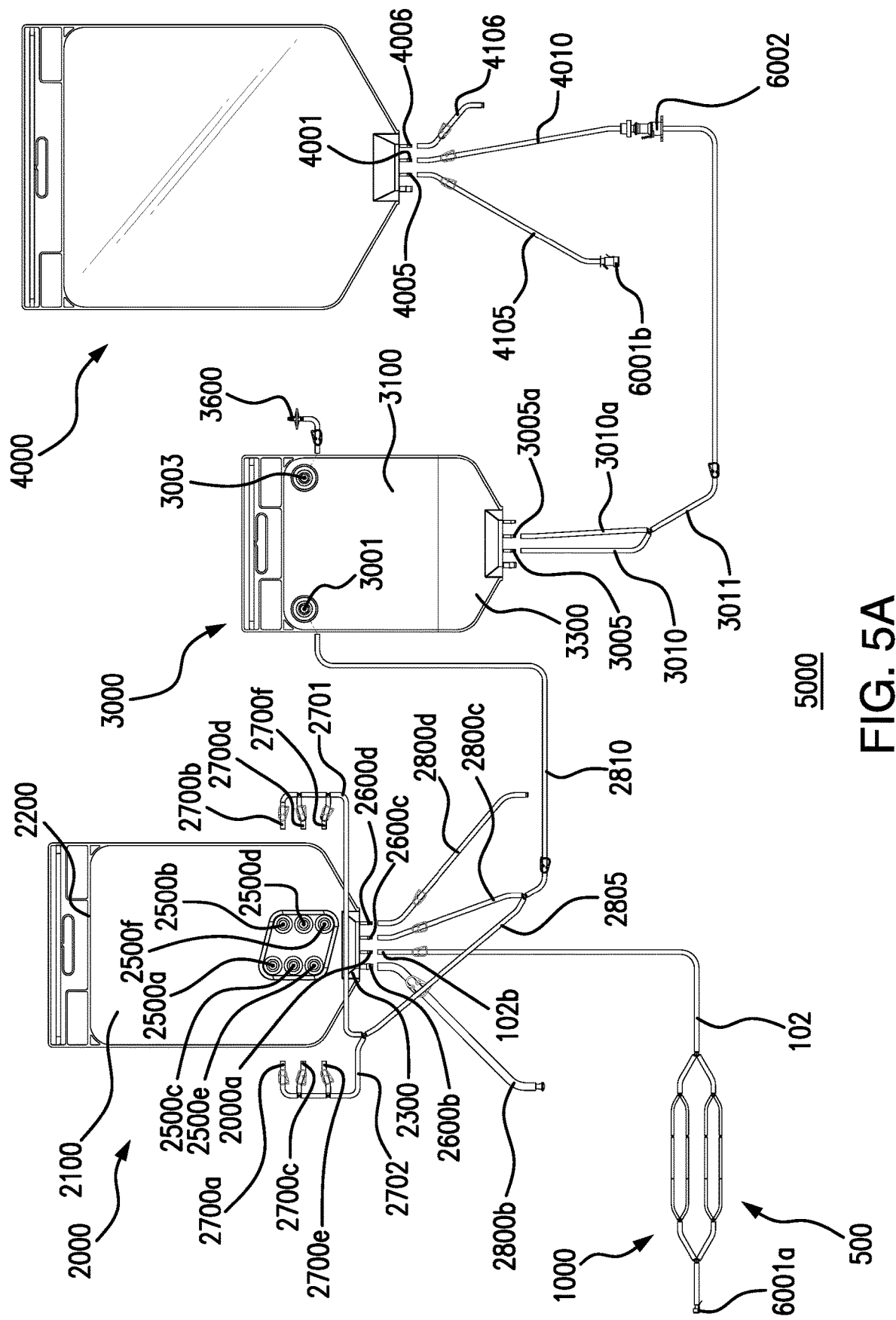
Figure 5B:
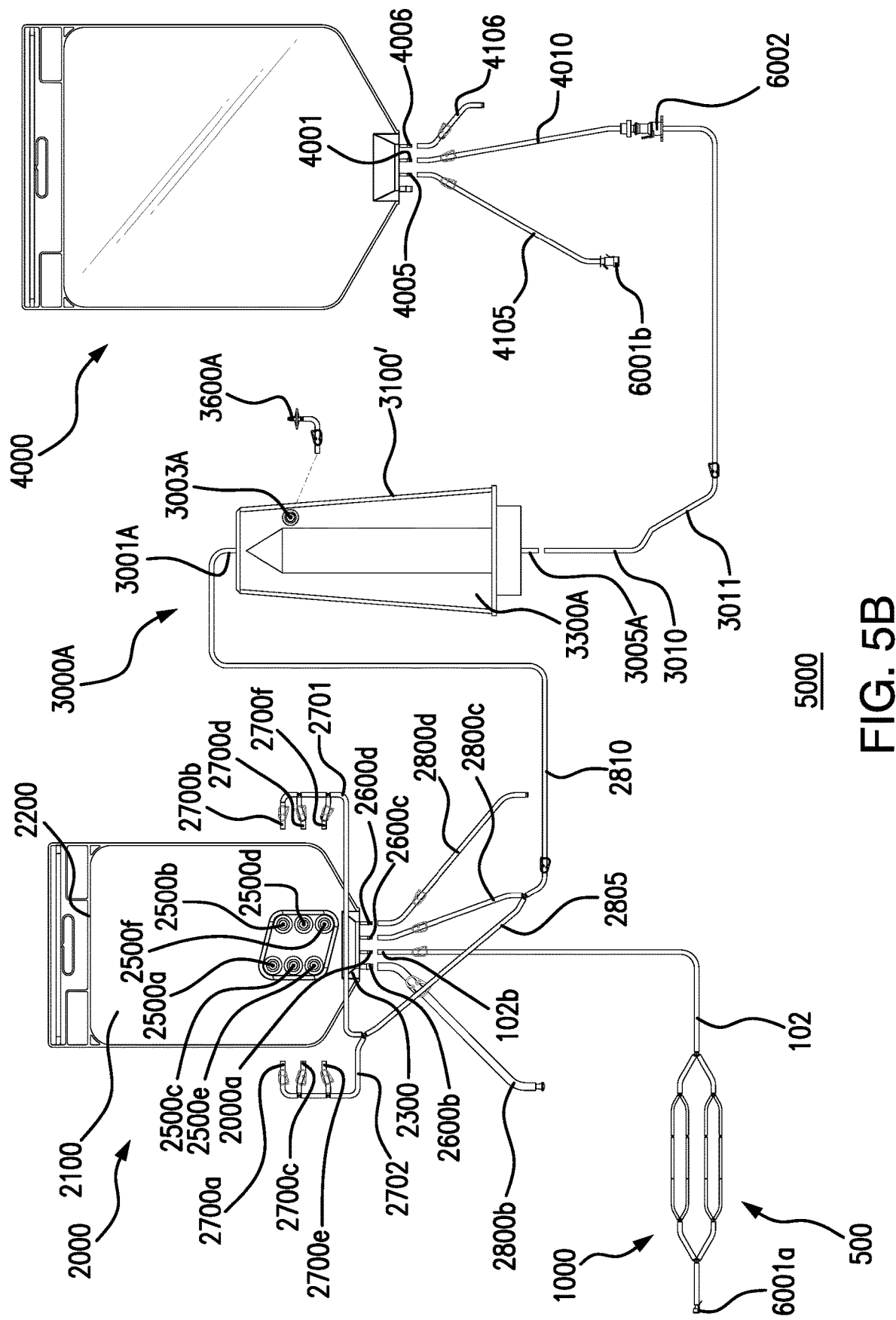

FIG. 5A is an embodiment of a cell separation system according to an embodiment of the invention, including a cell separation device, a cell settling device, a cell screening device (as illustrated in FIGS. 3A-3C), and a harvest container, in fluid communication via various conduits. FIG. 5B is an embodiment of a cell separation system according to an embodiment of the invention, including a cell separation device, a cell settling device, a cell screening device (as illustrated in FIG. 3D), and a harvest container, in fluid communication via various conduits.

DETAILED DESCRIPTION OF THE INVENTION

In accordance with an embodiment of the present invention, a cell separation system is provided, comprising A) a conduit for fluid communication with a source container, the source container comprising a fluid comprising cells, the conduit having a first end and a second end; B) a cell separation device comprising (a) an inlet having an inlet inner diameter, and an outlet having an outlet inner diameter, wherein the inlet is in fluid communication with the second end of the conduit for fluid communication with the source container; (b) a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter; C) a cell settling device comprising (a) a flexible bag having an interior volume, the flexible bag comprising at least two opposing side walls, each side wall having an interior surface and an exterior surface; a top end; a bottom end; and (b) a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least one port arranged at the bottom end of the bag, wherein the at least one port arranged at the bottom end of the bag is in fluid communication with the outlet of the cell separation device; and, D) a cell screening device comprising (a) a flexible bag having an interior volume, the flexible bag comprising at least two opposing side walls, each side wall having an interior surface and an exterior surface; a top end; a bottom end; and (b) a porous element comprising a screen having a nominal mesh size of at least about 30 micrometers arranged in the interior volume of the flexible bag, the screen forming a pouch having an open end and a closed end; (c) a plurality of ports in fluid communication with the interior volume of the flexible bag, the ports allowing fluid to pass into and/or out of the bag, the plurality of ports including at least one inlet port arranged in one of the opposing side walls and passing through the side wall, and at least one outlet port arranged at the bottom end of the bag; the inlet port being in fluid communication with one of the plurality of ports arranged in one of the opposing side walls of the flexible bag of the cell settling device; wherein the cell screening device is arranged to allow fluid comprising cells and microcarriers to pass from one of the plurality of ports arranged in one of the opposing side walls of the flexible bag of the cell settling device and through the inlet port into the interior volume of the cell screening device flexible bag, the cells passing through the open end and closed end of the screen pouch and through the outlet port and along an outlet conduit, the microcarriers being retained at the closed end of the screen pouch; or a cell screening device comprising (a) a housing having an interior volume; and (b) a porous element arranged in the interior volume of the housing, the porous element having a pore structure allowing fluid comprising cells to pass therethrough, but preventing the passage of microcarriers therethrough; (c) a plurality of ports in fluid communication with the interior volume of the housing, the ports allowing fluid to pass into and/or out of the housing, the plurality of ports including at least one inlet port, and at least one outlet port arranged at the bottom end of the housing; wherein the cell screening device is arranged to allow fluid comprising cells and microcarriers to pass through the inlet port into the interior volume of the housing, the cells passing through the porous element and through the outlet port, the microcarriers being retained by the porous element.

In another embodiment, a cell separation device is provided, comprising (a) an inlet having an inlet inner diameter, and an outlet having an outlet inner diameter; (b) a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths comprising a plurality of conduits fluidly connected by one or more connectors, each connector having at least one internal diameter, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths comprising a plurality of conduits fluidly connected by one or more connectors, each connector having at least one internal diameter, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter. In a preferred embodiment, the inlet inner diameter equals the outlet inner diameter.

In yet another embodiment, a cell settling device is provided, comprising (a) a flexible bag having an interior volume, the flexible bag comprising at least two opposing side walls, each side wall having an interior surface and an exterior surface; a top end; a bottom end; and (b) a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least one port arranged at the bottom end of the bag.

In a preferred embodiment of the cell settling device, the plurality of ports includes at least two additional ports arranged in at least one of the opposing side walls and passing through the side wall(s), wherein each of the two additional ports is arranged at a different predetermined height from the bottom end of the flexible bag, the predetermined height being different than the predetermined height of any other port arranged in at least one of the opposing side walls from the bottom end of the flexible bag. In some embodiments, the plurality of ports further includes at least one additional port arranged at the bottom end of the bag.

In an additional embodiment, a cell screening device comprises at least one inlet port and at least one outlet port, an interior volume, and a porous element between the at least one inlet port and the at least one outlet port, the ports allowing fluid to pass into and/or out of the cell screening device, wherein the cell screening device is arranged to allow fluid comprising cells and microcarriers to pass through the inlet port into the interior volume of the cell screening device, the cells passing through the porous element and through the outlet port, the microcarriers being retained by the porous element.

Illustratively, in one embodiment, the cell screening device comprises (a) a flexible bag having an interior volume, the flexible bag comprising at least two opposing side walls, each side wall having an interior surface and an exterior surface; a top end; a bottom end; and (b) a porous element comprising a screen having a nominal mesh size of at least about 30 micrometers arranged in the interior volume of the flexible bag, the screen forming a pouch having an open end and a closed end; (c) a plurality of ports in fluid communication with the interior volume of the flexible bag, the ports allowing fluid to pass into and/or out of the bag, the plurality of ports including at least one inlet port arranged in one of the opposing side walls and passing through the side wall, and at least one outlet port arranged at the bottom end of the bag; wherein the cell screening device is arranged to allow fluid comprising cells and microcarriers to pass through the inlet port into the interior volume of the bag, the cells passing through the open end and closed end of the screen pouch and through the outlet port, the microcarriers being retained at the closed end of the screen pouch.

In another illustrative embodiment, the cell screening device comprises (a) a housing having an interior volume; and a (b) porous element arranged in the interior volume of the housing, the porous element having a pore structure allowing fluid comprising cells to pass therethrough, but preventing the passage of microcarriers therethrough; (c) a plurality of ports in fluid communication with the interior volume of the housing, the ports allowing fluid to pass into and/or out of the housing, the plurality of ports including at least one inlet port, and at least one outlet port arranged at the bottom end of the housing; wherein the cell screening device is arranged to allow fluid comprising cells and microcarriers to pass through the inlet port into the interior volume of the housing, the cells passing through the porous element and through the outlet port, the microcarriers being retained by the porous element.

In accordance with embodiments of methods according to the invention, a method of separating cells from microcarriers comprises passing a fluid comprising cells attached to microcarriers through an embodiment of the cell separation device; and a method of separating cells from microcarrriers and harvesting the separated cells comprises passing a fluid comprising cells attached to microcarriers through an embodiment of the cell separation system.

In an embodiment, a method of separating cells from microcarrriers comprises passing a fluid comprising cells attached to microcarriers into an inlet of a cell separation device, the inlet having an inlet inner diameter, the cell separation device further comprising an outlet having an outlet inner diameter; a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths comprising a plurality of conduits fluidly connected by one or more connectors, each connector having at least one internal diameter, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths comprising a plurality of conduits fluidly connected by one or more connectors, each connector having at least one internal diameter, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter; passing a first portion of the fluid and a second portion of the fluid through the cell shear device, including (a) passing the first portion of the fluid along the first flow path such that separate sub-portions of the first portion of the fluid pass along at the least two separate first fluid sub-flow paths wherein cells are detached from microcarrriers; and (b) passing the second portion of the fluid along the second flow path such that separate sub-portions of the first portion of the fluid pass along at the least two separate first fluid sub-flow paths wherein cells are detached from microcarrriers; and passing detached cells and microcarriers through the outlet of the cell separation device.

In a preferred embodiment of the method, the method further comprising passing detached cells and microcarriers into an embodiment of a cell settling device having a plurality of ports positioned at various heights on the front of the cell settling device for more efficient detached cell and microcarrier separation. In an embodiment, fluid having an increased concentration of detached cells and some microcarriers is passed from the appropriate port into an embodiment of a cell screening device including a porous element therein, such that detached cells pass through the porous element and through an outlet port of the cell screening device, and into a harvest container, and microcarriers are retained within the cell screening device.

In another embodiment, a method of separating cells from microcarrriers and harvesting the separated cells comprises passing a fluid comprising cells attached to microcarriers through an embodiment of the cell separation system, wherein the system comprises A) a conduit for fluid communication with a source container, the source container comprising a fluid comprising cells, the conduit having a first end and a second end; B) a cell separation device comprising (a) an inlet having an inlet inner diameter, and an outlet having an outlet inner diameter, wherein the inlet is in fluid communication with the second end of the conduit for fluid communication with the source container; (b) a cell shear device, interposed between, and in fluid communication with, the inlet and the outlet, the shear device comprising a plurality of fluidly connected conduits arranged to provide at least a first fluid flow path and a second fluid flow path; (i) the first fluid flow path comprising a first fluid flow path inlet and a first fluid flow path outlet, and at least two separate first fluid sub-flow paths, wherein the at least two separate first fluid sub-flow paths are joined at a first fluid sub-flow path inlet and a first fluid sub-flow path outlet; (ii) the second fluid flow path comprising a second fluid flow path inlet and a second fluid flow path outlet, and at least two separate second fluid sub-flow paths, wherein the at least two separate second fluid sub-flow paths are joined at a second fluid sub-flow path inlet and a second fluid sub-flow path outlet; wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter; C) a cell settling device comprising (a) a flexible bag having an interior volume, the flexible bag comprising at least two opposing side walls, each side wall having an interior surface and an exterior surface; a top end; a bottom end; and (b) a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least one port arranged at the bottom end of the bag, wherein the at least one port arranged at the bottom end of the bag is in fluid communication with the outlet of the cell separation device; and, D) a cell screening device comprising (a) a flexible bag having an interior volume, the flexible bag comprising at least two opposing side walls, each side wall having an interior surface and an exterior surface; a top end; a bottom end; and (b) a porous element comprising a screen having a nominal mesh size of at least about 30 micrometers arranged in the interior volume of the flexible bag, the screen forming a pouch having an open end and a closed end; (c) a plurality of ports in fluid communication with the interior volume of the flexible bag, the ports allowing fluid to pass into and/or out of the bag, the plurality of ports including at least one inlet port arranged in one of the opposing side walls and passing through the side wall, and at least one outlet port arranged at the bottom end of the bag; the inlet port being in fluid communication with one of the plurality of ports arranged in one of the opposing side walls of the flexible bag of the cell settling device; wherein the cell screening device is arranged to allow fluid comprising cells and microcarriers to pass from one of the plurality of ports arranged in one of the opposing side walls of the flexible bag of the cell settling device and through the inlet port into the interior volume of the cell screening device flexible bag, the cells passing through the open end and closed end of the screen pouch and through the outlet port and along an outlet conduit, the microcarriers being retained at the closed end of the screen pouch; or a cell screening device comprising (a) a housing having an interior volume; and a (b) porous element arranged in the interior volume of the housing, the porous element having a pore structure allowing fluid comprising cells to pass therethrough, but preventing the passage of microcarriers therethrough; (c) a plurality of ports in fluid communication with the interior volume of the housing, the ports allowing fluid to pass into and/or out of the housing, the plurality of ports including at least one inlet port, and at least one outlet port arranged at the bottom end of the housing; wherein the cell screening device is arranged to allow fluid comprising cells and microcarriers to pass through the inlet port into the interior volume of the housing, the cells passing through the porous element and through the outlet port, the microcarriers being retained by the porous element; the method comprising passing a fluid comprising cells attached to microcarriers into the inlet of the cell separation device, passing a first portion of the fluid and a second portion of the fluid through the cell shear device, including (a) passing the first portion of the fluid along the first flow path such that separate sub-portions of the first portion of the fluid pass along at the least two separate first fluid sub-flow paths wherein cells are detached from microcarrriers; and (b) passing the second portion of the fluid along the second flow path such that separate sub-portions of the first portion of the fluid pass along at the least two separate first fluid sub-flow paths wherein cells are detached from microcarrriers; and passing detached cells and microcarriers through the outlet of the cell separation device into an embodiment of a cell settling device having a plurality of ports positioned at various heights on the front of the cell settling device; passing fluid comprising detached cells and some microcarriers from the appropriate port into an embodiment of a cell screening device including a porous element therein, such that detached cells pass through the element and through an outlet port of the cell settling device into a harvest container, while retaining microcarriers within the pouch.

In some embodiments, the method further comprises passing detached cells from the harvest container into a cell concentration device such as a centrifuge, hollow fiber device, a tangential flow device, or another bioreactor), and further concentrating the detached cells. Alternatively, or additionally, in some embodiments, the method further comprises passing detached cells from the harvest container through a sampling port and determining the concentration of the cells in the harvest container. For example, the concentration of cells in the harvest container can be determined before passing detached cells into a cell concentration device.

Advantageously, the shear device imparts gentle shear to the microcarrier/cell slurry to detach the cells from the microcarriers while minimizing damage to the cells. Additionally, aggregated cells can be separated by the shear. A suspension of single cells can be produced and the cells can be harvested for further use. In some applications, cells can be separated without the use of enzymes, or with a reduced concentration of enzymes.

A variety of different types of cells can be separated and harvested according to embodiments of the invention. Particularly suitable applications are for separation and harvesting of adherent cells grown on microcarriers that can be used in seed train cell expansion for seeding larger bioreactors or for isolation of cells used in cell and gene therapy applications. Suitable cells include, but are not limited to CHO, BHK21, HEK293, Vero, MDCK, primary chondrocytes, primary liver, primary renal, bone marrow-derived mesenchymal stem/stromal cells, adipose-derived mesenchymal stem/stromal cells, embryonic stem cells, and induced pluripotent stem cells.

A variety of microcarriers (beads) can be used according to embodiments of the invention, and suitable microcarriers can be selected by one of skill in the art. Microcarriers typically are provided with a nominal size range which is specific for each product type. They can be composed of multiple different materials including, rigid polymers, biodegradable substances (For example; cellulose, fibrinogen, alginate or pectin), glass and others.

Each of the components of the invention will now be described in more detail below, wherein like components have like reference numbers.

FIGS. 1A and 1B show an illustrative embodiment of the cell separation device 1000, wherein the cell separation device comprises an inlet 100 (illustrated as comprising a connector such as a 3 branch Y-connector connected to conduits (e.g., flexible plasticized tubing) 101, 511', and 521') having an inlet inner diameter 100a, and an outlet 200 (illustrated as comprising a connector such as a 3 branch Y-connector connected to conduits (e.g., flexible plasticized tubing) 512', 522', and 102) having an outlet inner diameter 200a; a cell shear device 500, interposed between, and in fluid communication with, the inlet and the outlet, the shear device comprising a plurality of fluidly connected conduits 515a, 516a, 517a; 515b, 516b, 517b; 525a, 526a, 527a; 525b, 526b, and 527b (e.g., flexible plasticized tubing) arranged to provide at least a first fluid flow path 501 and a second fluid flow path 502, each of the fluidly connected conduits having a conduit inner diameter; the first fluid flow path 501 comprising a first fluid flow path inlet 511 (illustrated as a branch of inlet 100) and a first fluid flow path outlet 512 (illustrated as a branch of outlet 200), and at least two separate first fluid sub-flow paths 510a, 510b, wherein the at least two separate first fluid sub-flow paths are joined at a first fluid sub-flow path inlet 510 and a first fluid sub-flow path outlet 510'; the second fluid flow path 502 comprising a second fluid flow path inlet 521 (illustrated as a branch of inlet 100) and a second fluid flow path outlet 522 (illustrated as a branch of outlet 200), and at least two separate second fluid sub-flow paths 520a, 520b, wherein the at least two separate second fluid sub-flow paths are joined at a second fluid sub-flow path inlet 520 and a second fluid sub-flow path outlet 520'; wherein a portion in each of the separate fluid sub-flow paths has an inner diameter that is less than each of the inlet inner diameter 100a and the outlet inner diameter 200a.

In this illustrated embodiment, each of the branches of inlet 100 and outlet 200 has the same inner diameter (including first fluid flow path inlet 511 connecting with conduit 511'; second fluid flow path inlet 521 connecting with conduit 521'; first fluid flow path outlet 512 connecting with conduit 512'; and second fluid flow path outlet 522 connecting with conduit 522'), wherein that inner diameter is also the same as the inner diameter of the branch of first fluid sub-flow path inlet 510 connecting with conduit 511', the branch of second fluid sub-flow path inlet 520 connecting with conduit 521', the branch of first fluid sub-flow path outlet 510' connecting with conduit 512', and the branch of second fluid sub-flow path outlet 520' connecting with conduit 522'. This inner diameter is larger than the inner diameters of the other branches of 510, 520, 510', and 520', wherein these other branches each have the same, though smaller, inner diameters.

In some embodiments, each of the fluid sub-flow paths includes at least one connector (preferably, a first reducing connector, having an internal diameter, in the direction of fluid flow, larger at the inflow end than at the outflow end) connecting conduits between the first fluid sub-flow path inlet and first fluid sub-flow path outlet and between the second fluid sub-flow path inlet and second fluid sub-flow path outlet, respectively. In some embodiments, each of the fluid sub-flow paths includes at least one second reducing connector, having an internal diameter, in the direction of fluid flow, smaller at the inflow end than at the outflow end, connecting conduits between the first fluid sub-flow path inlet and first fluid sub-flow path outlet and between the second fluid sub-flow path inlet and second fluid sub-flow path outlet, respectively For example, in the illustrated embodiment, first fluid sub-flow path 510a includes a first reducing connector 513a (having a larger internal diameter at the inflow end than at the outflow end) and a second reducing connector 514a (having a smaller internal diameter at the inflow end than at the outflow end), and first fluid sub-flow path 510b includes a first reducing connector 513b (having a larger internal diameter at the inflow end than at the outflow end) and a second reducing connector 514b (having a smaller internal diameter at the inflow end than at the outflow end); and similarly, second fluid sub-flow path 520a includes a first reducing connector 523a (having a larger internal diameter at the inflow end than at the outflow end) and a second reducing connector 524a (having a smaller internal diameter at the inflow end than at the outflow end), and second fluid sub-flow path 520b includes a first reducing connector 523b (having a larger internal diameter at the inflow end than at the outflow end) and a second reducing connector 524b (having a smaller internal diameter at the inflow end than at the outflow end).

Preferably, the inlet inner diameter 100a equals the outlet inner diameter 200a.

While the embodiment of the cell separation device illustrated in FIG. 1 has first and second fluid flow paths, each flow path comprising two separate fluid sub-flow paths, embodiments of the cell separation device can have any number of a plurality of fluid flow paths and/or fluid sub-flow paths.

The cell separation device can include additional components such as any one or more of any of the following: one or more additional connectors, one or more additional conduits and/or one or more flow control devices such as clamps.

In the illustrated embodiment, the cell separation device further comprises a conduit 101 in fluid communication with the inlet 100, wherein the conduit can be placed in fluid communication with a source container containing a fluid to be processed, typically, the source container comprises a bioreactor containing a fluid comprising cells and microcarriers (source container not shown). The illustrated conduit 101 has a first end 101a and a second end 101b, wherein the second end is connected to the inlet 100, and the first end comprises a sterile connection device 6001a.

The illustrated embodiment further comprises an additional conduit 102 in fluid communication with the outlet 200, wherein the conduit can be placed in fluid communication with a settling device 2000, which receives the detached cells and the microcarriers passing from the shear device 500 and through the outlet 200. The illustrated conduit 102 has a first end 102a and a second end 102b, wherein the first end is connected to the outlet 200, and the second end communicates with, and is attached to, port 2600a of the settling device 2000.

Figure 2A:
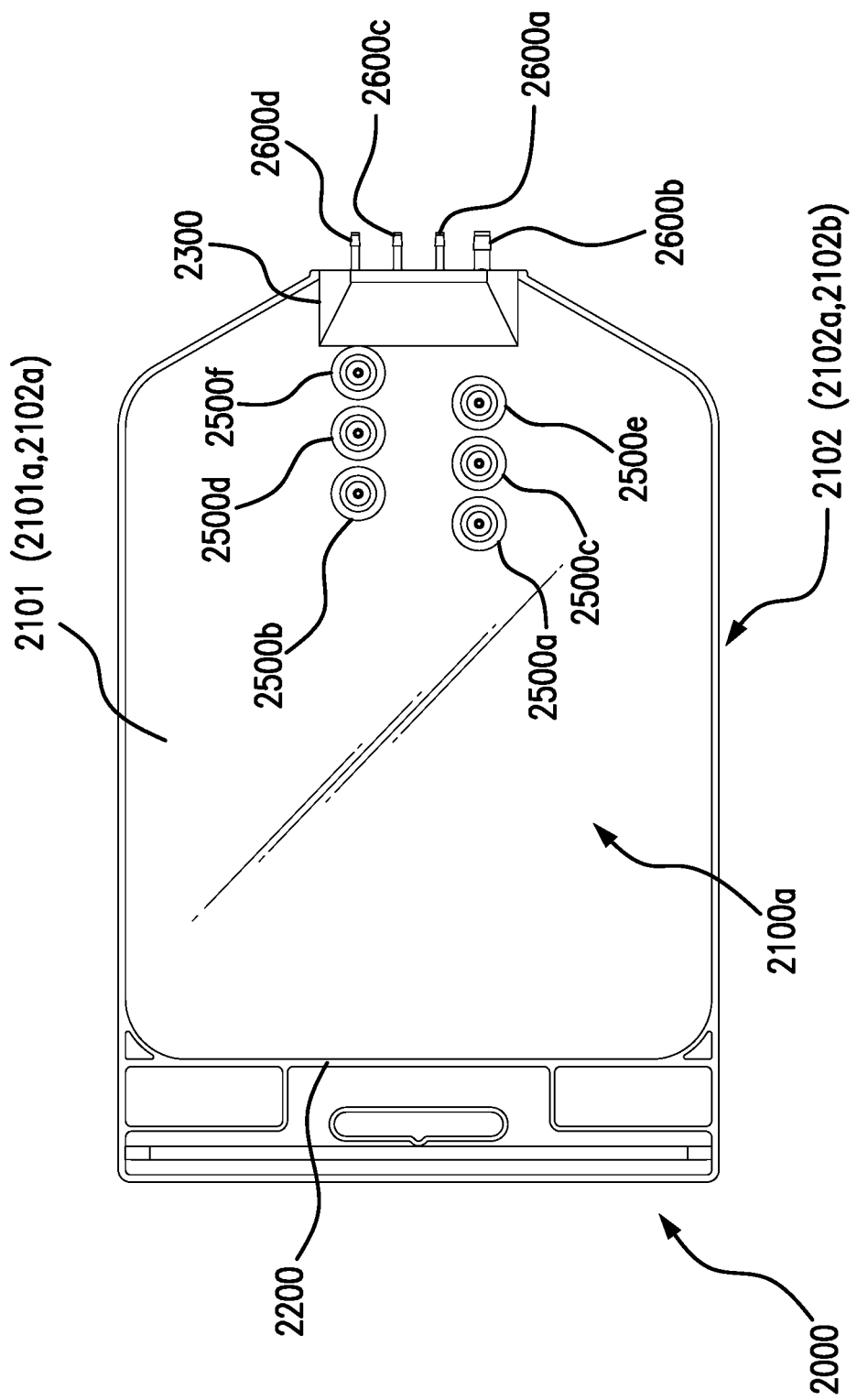
FIG. 2A is a top view of an embodiment of a cell settling device according to the present invention.

FIGS. 2A and 2B show an illustrative embodiment of the settling device 2000, wherein the cell settling device comprise a flexible bag 2100 having an interior volume 2100a, the flexible bag comprising at least two opposing side walls 2101, 2102, each side wall having an interior surface 2101a, 2102a and an exterior surface 2101b, 2102b; a top end 2200; a bottom end 2300; and a plurality of ports in fluid communication with the interior volume of the flexible bag, the ports allowing fluid to pass into and/or out of the bag, the plurality of ports including two or more ports arranged in at least one of the opposing side walls and passing through the side wall(s), wherein each of the two or more ports is arranged at a different predetermined height from the bottom end of the flexible bag; the plurality of ports also including at least two ports arranged at the bottom end of the bag.

Advantageously, the ports are arranged at different predetermined heights from the bottom end of the flexible bag for more efficient processing of different amounts of microcarrier/cell mixtures, wherein cells are separated from microcarriers by gravity-based differential settling.

Preferably, the plurality of ports includes at least two additional ports arranged in at least one of the opposing side walls and passing through the side wall(s), wherein each of the two additional ports is arranged at a different predetermined height from the bottom end of the flexible bag, the predetermined height being different than the predetermined height of any other port arranged in at least one of the opposing side walls from the bottom end of the flexible bag. In the illustrated embodiment, the settling device 2000 has 6 ports, 2500a, 2500b, 2500c, 2500d, 2500e, and 2500f, each arranged at a different predetermined height from the bottom end of the flexible bag.

As noted above, the ports are arranged at different predetermined heights from the bottom end of the flexible bag for more efficient processing of different amounts of microcarrier/cell mixtures. The following exemplary table illustrates amounts of different size microcarriers processed using different ports arranged at different predetermined heights from the bottom end of a flexible bag, based on the bag having a maximum liquid volume of 16.7 L and a maximum microcarrier amount of 3.3 KG. Other predetermined heights from the bottom end, amounts of microcarriers, sizes of microcarriers, and bag volumes, are suitable.

TABLE

| Port height from bottom of bag (mm) | 125-212 µm size beads (grams) | 90-150 µm size beads (grams) | 160-200 µm size beads (grams) |
|---|---|---|---|
| 75 | 500 | 500 | 300 |
| 100 | 700 | 700 | 500 |
| 125 | 1400 | 1400 | 700 |
| 150 | 2000 | 2000 | 1400 |
| 175 | 2800 | 2800 | 2000 |
| 200 | 3333 | 3333 | 2800 |

In the illustrated embodiment of the cell settling device, the plurality of ports further include at least two additional ports arranged at the bottom end of the bag. In the illustrated embodiment, settling device includes four additional ports, 2600a, 2600b, 2600c, and 2600d, arranged at the bottom end 2300 of the bag. Illustratively, port 2600b can comprise an enzyme quenching fluid inlet port, and port 2600d can comprise a sampling port.

When included as part of a system (e.g., as shown in FIGS. 5A and 5B), each of the ports of the cell settling device communicates with a conduit, and various conduits are placed in communication with each other (e.g., via connectors). For example, in the exemplary system 5000, 5000A shown in FIGS. 5A and 5B, ports 2500a, 2500b, 2500c, 2500d, 2500e, and 2500f, are attached to conduits 2700a, 2700b, 2700c, 2700d, 2700e, and 2700f, respectively; conduits 2700a, 2700c, and 2700e communicate with conduit 2702, and conduits 2700b, 2700d, and 2700f communicate with conduit 2701, conduits 2701 and 2702 are communicate in turn with conduit 2805, port 2600c is attached to conduit 2800c, wherein conduits 2805 and 2800c communicate with conduit 2810.

The cell screening device (or cell cell/microcarrier separation device) is arranged to separate the microcarriers from the cells in the fluid. Embodiments of the cell screening device can have a variety of configurations, wherein the device includes a porous element having a porous structure less than the diameter of the microcarrier beads, such that the beads do not pass through the porous element, while fluid containing cells passes through the element. Illustratively, the porous structure can be as a pore size (for example, as evidenced by bubble point, or by $K_L$ as described in, for example, U.S. Pat. No. 4,340,479, or evidenced by capillary condensation flow porometry), a mean flow pore (MFP) size (e.g., when characterized using a porometer, for example, a Porvair Porometer (Porvair plc, Norfolk, UK), or a porometer available under the trademark POROLUX (Porometer.com; Belgium)), a pore rating, a pore diameter (e.g., when characterized using the modified OSU F2 test as described in, for example, U.S. Pat. No. 4,925,572), or removal rating media. The porous element can comprise a screen, mesh, membrane, fibrous medium (woven or non-woven), or a combination of any two or more of these. A variety of porous elements (and filter devices including porous elements) are suitable, including those commercially available from Pall Corporation (Port Washington, N.Y.). Porous elements can have a variety of configurations, including planar, pleated, and hollow cylindrical.

FIGS. 3A, 3B, and 3C, show an illustrative embodiment of the cell screening device (or cell cell/microcarrier separation device) 3000 for separating the microcarriers from the cells in the fluid, wherein the cell screening device comprises a flexible bag 3100 having an interior volume 3100a, the flexible bag comprising at least two opposing side walls 3101, 3102, each side wall having an interior surface 3101a, 3102a, and an exterior surface 3101b, 3102b; a top end 3200; a bottom end 3300; and a porous element 3500 having a nominal pore size (for a screen, having a nominal mesh size) less than the diameter of the microcarrier beads, such that the beads do not pass through the screen, wherein the screen 3500 is arranged in the interior volume of the flexible bag, the screen forming a pouch having an open end 3501 and a closed end 3502 (as shown particularly in FIG. 3C). While the suitable nominal pore size/nominal mesh size can be determined by one of ordinary skill in the art, it is typically at least about 30 micrometers. Illustratively, for beads having a nominal size (diameter) of about 40 to about 75 micrometers, the pore size can be, for example, about 30 micrometers; for beads having a nominal size (diameter) of about 90 to about 125 micrometers, the pore size can be, for example, about 30 to about 50 micrometers; for beads having a nominal size (diameter) of about 125 to about 212 micrometers, the pore size can be, for example, about 30 to about 70 micrometers; for beads having a nominal size (diameter) of about 200 to about 400 micrometers, the pore size can be, for example, about 30 to about 100 micrometers; and for beads having a nominal size (diameter) of about 400 to about 1000 micrometers, the pore size can be, for example, about 30 to about 300 micrometers.

In the embodiment illustrated in FIG. 3D, the cell screening device 3000A comprises a filter device 3100A having an interior volume 3100'; a top end 3200A; a bottom end 3300A; and a filter 3510A comprising a porous element 3500A (illustrated here as having a hollow cylindrical configuration). In this illustrated embodiment, the filter device comprises a housing having an inlet port 3001A and an outlet port 3005 and defining a fluid flow path between the inlet port and the outlet port, with the filter 3510A comprising a porous element 3500A disposed in the housing across the fluid flow path. While the suitable pore structure can be determined by one of ordinary skill in the art, it is typically at least about 30 micrometers. Illustratively, for beads having a nominal size (diameter) of about 40 to about 75 micrometers, the pore size, pore rating, or pore diameter can be, for example, about 30 micrometers; for beads having a nominal size (diameter) of about 90 to about 125 micrometers, the pore size, pore rating, or pore diameter can be, for example, about 30 to about 50 micrometers; for beads having a nominal size (diameter) of about 125 to about 212 micrometers, the pore size, pore rating, or pore diameter can be, for example, about 30 to about 70 micrometers; for beads having a nominal size (diameter) of about 200 to about 400 micrometers, the pore size, pore rating, or pore diameter can be, for example, about 30 to about 100 micrometers; and for beads having a nominal size (diameter) of about 400 to about 1000 micrometers, the pore size, pore rating, or pore diameter can be, for example, about 30 to about 300 micrometers.

Embodiments of the cell screening device further comprise a plurality of ports in fluid communication with the interior volume of the screening device, the ports allowing fluid to pass into and/or out of the device.

In accordance with the embodiment illustrated in FIGS. 3A-3C, the plurality of ports including at least one inlet port 3001 arranged in one of the opposing side walls and passing through the side wall, and at least one outlet port 3005 arranged at the bottom end of the bag connected to conduit 3010 (in turn communicating with conduit 3011), wherein the illustrated embodiment shows a second outlet port 3005a connected to conduit 3010a (in turn also communicating with conduit 3011); wherein the cell screening device is arranged to allow fluid comprising cells and microcarriers to pass through the inlet port into the interior volume of the bag, the cells passing through the open end and closed end of the screen pouch and through the outlet port(s), the microcarriers being retained by the screen, e.g., at the closed end of the screen pouch. In some embodiments, the use of at least one additional outlet port reduces hold up volume for larger scale applications.

In accordance with the embodiment illustrated in FIG. 3D, the plurality of ports includes at least one inlet port 3001A, and at least one outlet port 3005A arranged at the bottom end of the filter device connected to conduit 3010 (in turn communicating with conduit 3011); wherein the cell screening device is arranged to allow fluid comprising cells and microcarriers to pass through the inlet port into the interior volume of the filter (illustrated by curved arrows), the cells passing through the porous element and through the outlet port (illustrated by a straight arrow), the microcarriers being retained in the screening device by the porous element.

In the illustrated embodiments, the cell screening devices further comprises a vent port 3003, 3003A in fluid communication with a vent device 3600, 3600A (shown in FIGS. 5A and 5B) comprising a housing having a housing inlet and a housing outlet and defining a fluid flow path between the inlet and the outlet and a microporous membrane disposed in the housing across the fluid flow path, the microporous membrane having a bacterial blocking pore rating (e.g., of about 0.2 micrometers). In some embodiments, the use of a vent is desirable in order to prevent pressure build up in the cell screening device during processing.

The cells passing through the outlet port(s) of the screen device are passed via conduit 3010 (and 3010a if present) and conduit 3011 into the harvest container 4000 as shown in FIG. 4 (preferably comprising a flexible bag as illustrated as part of the embodiment of the cell separation system 5000, 5000A shown in FIGS. 5A and 5B). While a variety of containers are suitable, in the illustrated embodiments the harvest container comprises a flexible bag 4100 having an interior volume 4100a, the flexible bag comprising at least two opposing side walls 4101, 4102, each side wall having an interior surface 4101a, 4102a and an exterior surface 4101b, 4102b; a top end 4200; a bottom end 4300; and a plurality of ports in fluid communication with the interior volume of the flexible bag, the ports allowing fluid to pass into and/or out of the bag. In the illustrated embodiment, the bag has a plurality of ports arranged at the bottom end of the bag, the plurality of ports including an inlet port 4001 (for fluid communication with the cell screening device), and at least one outlet port 4005 (e.g., for passage to a cell concentration device such as a centrifuge, hollow fiber device, a tangential flow device, or another bioreactor), and a sampling port 4006 (e.g., for determining the concentration of the cells in the harvest container). In the embodiment illustrated in FIG. 5, port 4005 is connected to conduit 4105, and port 4106 is connected to conduit 4106.

A variety of materials are suitable for use in producing the components of systems according to embodiments of the invention. A wide variety of conduits, connectors, flow control devices (e.g., clamps and/or valves) and vents are known in the art. Flexible bags and conduits can be made from, for example, from plasticized polyvinyl chloride; ethylene butyl acrylate copolymer (EBAC) resin; ethylene methyl acrylate copolymer (EMAC) resin; plasticized ultra-high-molecular weight PVC resin; ethylene vinyl acetate (EVA). The bags and/or conduits can also be formed from, for example, polyolefin, polypropylene, polyurethane, polyester, and polycarbonate and combinations of materials.

The system as used is "closed," allowing the processing of fluid without the need to compromise the sterile integrity of the system. A closed system can be as originally made, or result from the connection of system components using a variety of devices known in the art. Preferably, the system includes sterile connection devices and sterile disconnection devices for connecting and disconnecting various elements of the system and/or for connecting elements of the system to, for example, cell source containers.

For example, FIGS. 5A and 5B show sterile connection devices 6001a and 6001b, as well as sterile disconnection device 6002.

A variety of sterile connection and disconnection devices are suitable. For example, sterile connection devices available under the names KLEENPACK Presto Sterile Connector, KLEENPACK Sterile Connectors, and KLEENPACK II Sterile Connectors, and/or sterile disconnection devices under the name KLEENPACK Sterile Disconnectors (Pall Corporation, Port Washington, N.Y.) can be used.

The following example further illustrates the invention but, of course, should not be construed as in any way limiting its scope.

EXAMPLE

This example demonstrates separating and harvesting mesenchymal stem cells in accordance with an embodiment of the invention, using different culture volumes.

A sterile system is set up as generally illustrated in FIG. 5A wherein the settling bag is 20 L, the screen bag is 10 L, and the cell collection bag is 50 L. The bags and conduits are made from polypropylene. The screen bag has a screen with a pore size (in this case, a nominal mesh size) of about 50 micrometers. The cell separation device is sterilized by autoclaving at 121° C. for 30 minutes, and the system is assembled and subsequently sterilized using gamma-irradiation between 25-50 kGa.

The following table lists the culture volumes, microcarrier loads, enzyme volumes, enzyme quench volumes, settling bag volumes, settling bag front ports, total wash buffer volumes, and total cell collection bag volumes, in this Example.

| Run | Culture volume (mL) | MC load (gm) | Enzyme volume (mL) | Enzyme quench volume (mL) | Settling bag volume (mL) | Settling bag front port | Total Wash buffer volume (mL) | Total cell collection bag volume (mL) |
| --- | --- | --- | --- | --- | --- | --- | --- | --- |
| 1 | 10,000 | 417 | 4200 | 2500 | 8700 | Red | 5000 | 13700 |
| 2 | 10,000 | 417 | 1020 | 600 | 3650 | Red | 6000 | 9650 |
| 3 | 40,000 | 1667 | 4200 | 2400 | 11600 | Black | 19000 | 30600 |
| 4 | 50,000 | 2083 | 5250 | 3000 | 10750 | Black | 21000 | 31750 |

In this example, the cell separation device is connected to a bioreactor (PADREACTOR System; Pall Corporation, Port Washington, N.Y.) using an appropriately-size connector and the step down is adjusted to connect to ¼" diameter tubing 101. The ¼" ID tubing line is split into two equivalent fluid paths 501, 502 via ¼" hose barb (HB) Y connector 100. Each fluid path is subsequently split into two additional fluid paths (510a, 510b; 520a, 520b) via ¼" to ⅛" HB reducing Y connectors 510, 520. Each of the total four fluid paths contains two straight reducing connectors ⅛"×³⁄₃₂" (513a, 514a; 513b, 514b; 523a, 524a; 523b, 524b) which are placed 10 cm apart. Two of the four fluid paths are recombined via a ⅛" to ¼" HB Y connector 510' and the remaining two are connected in the same fashion via 520'. The two fluid paths are connected via a ¼" HB Y connector 200 to the ¼" line 102 connecting to the settling bag for the next process.

Each of conduits 101, 511', 521', 512', 522', and 102 has the same conduit internal diameter, and each of conduits 515a, 516a, 517a; 515b, 516b, 517b; 525a, 526a, 527a; 525b, 526b, and 527b has the same conduit internal diameter, wherein the conduit internal diameter for each of conduits 101, 511', 521', 512', 522', and 102 is larger than the conduit internal diameter for each of conduits 515a, 516a, 517a; 515b, 516b, 517b; 525a, 526a, 527a; 525b, 526b, and 527b.

The settling bag has 6 ports on the side wall of the bag, with different colored clamps associated with the various ports. Starting from the lowest port on the side wall and moving upwards toward the top end of the bag, the respective ports have colored clamps and are arranged for processing the following amounts of cell/microcarrier (MC) mixture in grams: 500 (red clamp; port 2500f arranged at 75 mm height from the bottom of the bag), 700 (green clamp; port 2500e arranged at 100 mm height from the bottom of the bag), 1400 (yellow clamp; port 2500d arranged at 125 mm height from the bottom of the bag), 2000 (black clamp; port 2500c arranged at 150 mm height from the bottom of the bag), 2800 (blue clamp; port 2500b arranged at 175 mm height from the bottom of the bag), and 3333 (orange clamp; port 2500a arranged at 200 mm height from the bottom of the bag).

The sterile connections and disconnections are KLEEN-PACK Presto Sterile Connectors and KLEENPACK Sterile Disconnectors (Pall Corporation, Port Washington, N.Y.).

Peristaltic pumps are associated with the conduits providing fluid communication between the shear device and the settling bag, the settling bag and the screen bag, and between the screen bag and the cell collection bag. Clamps are associated with each conduit, and are initially closed.

The settling bag and the screen bag are hung at a height of about 4 feet, and the collection bag is placed flat on a work station surface.

The cell separation device provides for gentle shear to the microcarrier/cell slurry, such that cells are detached from the microcarriers and a single-cell suspension is generated while minimizing or avoiding cell death.

Operating pressure is ≤0.15 bar.

A container containing enzyme quenching solution (HY-CLONE, GE Healthcare Life Sciences, Logan, Utah) is sterile connected to settling bag 2000 via port 2600b, and the solution is transferred into the bag.

The bioreactor contains commercially available collagen coated plastic microcarrier beads (SOLOHILL microcarriers, Pall Corporation, Port Washington, N.Y.) having an average diameter of about 125-212 micrometers. Cell detachment enzyme is transferred into the bioreactor, and the agitation control is turned on, mixing the beads and enzyme at a constant speed.

Conduit 101 is connected to the harvest line of the bioreactor via sterile connectors, and conduit 102 is positioned in a peristaltic pump head (MASTERFLEX L/S Easy-Load II 77200-62 (Cole-Palmer Instrument Company, Vernon Hills, Ill.)), and the pump is set at a speed of 720 mL/min flow rate.

Clamps on the conduits between the bioreactor, the separation device, and the settling bag 2000 are opened, and all other clamps remain closed. The peristaltic pump is activated and the bead/cell/enzyme fluid slurry is transferred from the bioreactor through the separation device into the settling bag at 720 mL/min. The pump is turned off, all of the opened clamps are closed, and the contents in the bag are allowed to settle in the settling bag for about 5 minutes.

After the settling period, the clamp on the conduit connecting to port 2500f or 2500c (see table at beginning of Example) on the front of the bag is opened, as are the clamps on the conduits between port 2500f or 2500c, on the conduits communicating with port 3001 on the screen bag 3000, and on the conduits 3010, 3010a between ports 3005, 3005a (on the screen bag 3000), 3011, 4010 and port 4010 (on the harvest container 4000). All the other clamps are closed.

Conduit 2810 between the settling bag and the screen bag is positioned in another peristaltic pump head, and the pump is set at a speed of 1 L/min flow rate. The peristaltic pump is activated and the bead/cell suspension is transferred from the settling bag and into the screen bag at 1 L/min, wherein the cell-containing fluid passes through the screen, and the beads are retained in the screen pouch. The pump is turned off, all of the opened clamps are closed.

Wash buffer (Dulbecco's Phosphate-Buffered Solution) is added to the bioreactor, and agitated for about 5 minutes. Clamps on the conduits between the bioreactor, the separation device, and the settling bag 2000 are opened, the peristaltic pump is activated, and about half of the volume of wash buffer is transferred to from the bioreactor and through the separation device into the settling bag at a rate of 720 mL/min. The pump is turned off, all of the opened clamps are closed, the bag is manually massaged 5 times, and the bag contents are allowed to settle in the settling bag for about 5 minutes.

After the settling period, the clamp on the conduit connecting to port 2500f or 2500c on the front of the bag is opened, as are the clamps on the conduits between port 2500f or 2500c, on the conduits communicating with port 3001 on the screen bag 3000, and on the conduits 3010, 3010a between ports 3005, 3005a (on the screen bag 3000), 3011, 4010 and port 4010 (on the harvest container 4000). All the other clamps are closed.

Conduit 2810 between the settling bag and the screen bag is positioned in a peristaltic pump head, and the pump is set at a speed of 1 L/min flow rate. The peristaltic pump is activated and the bead/cell suspension is transferred from the settling bag and into the screen bag at 1 L/min, wherein the cell-containing fluid passes through the screen, and the beads are retained in the screen pouch. The pump is turned off, all of the opened clamps are closed.

Clamps on the conduits between the bioreactor, the separation device, and the settling bag 2000 are opened, the peristaltic pump is activated, and the other half of the volume of wash buffer is transferred to from the bioreactor and through the separation device into the settling bag at a rate of 720 mL/min. The pump is turned off, all of the opened clamps are closed, the bag is manually massaged 5 times.

The clamps on the conduit connected to port 2600c, as well as on conduits 2810, 3011, and 4010 are opened, all other clamps are closed.

Conduit 3011 between the screen bag and the harvest container is positioned in another peristaltic pump head.

The peristaltic pump associated with conduit 2810 is activated and the bead/cell suspension is transferred from the settling bag and into the screen bag at 720 mL/min, wherein the cell-containing fluid passes through the screen, and the beads are retained in the screen pouch. Simultaneously, the peristaltic pump associated with conduit 3011 is activated and the bead-free cell suspension is transferred from the screen bag and into the harvest container at 720 mL/min.

The peristaltic pumps are turned off, and all opened clamps are closed. The harvest connector is disconnected from the rest of the system by disconnecting the sterile disconnector 6002.

The harvest connector is subsequently sterile-connected to a cell concentration device wherein the cells are further concentrated.

The range of viable cell concentrations in this Example is about $5.00 \times 10^5$ to about $2.00 \times 10^6$ cells per ml.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cell separation system comprising:
   A) a conduit for fluid communication with a source container, the source container comprising a fluid comprising cells, the conduit having a first end and a second end;
   B) a cell separation device comprising
      (a) an inlet having an inlet inner diameter, and an outlet having an outlet inner diameter, wherein the inlet is in fluid communication with the second end of the conduit for fluid communication with the source container;
      (b) a cell shear device, interposed between, and in fluid communication with, the inlet and the outlet, the shear device comprising a plurality of fluidly connected conduits arranged to provide at least a first fluid flow path and a second fluid flow path;
         (i) the first fluid flow path comprising a first fluid flow path inlet and a first fluid flow path outlet, and at least two separate first fluid sub-flow paths, wherein the at least two separate first fluid sub-flow path are joined at a first fluid sub-flow path inlet and a first fluid sub-flow path outlet;
         (ii) the second fluid flow path comprising a second fluid flow path inlet and a second fluid flow path outlet, and at least two separate second fluid sub-flow paths, wherein the at least two separate second fluid sub-flow paths are joined at a second fluid sub-flow path inlet and a second fluid sub-flow path outlet;
      wherein at least one of the one or more connectors in each of the at least two separate first fluid sub-flow paths and in each of the at least two separate second fluid sub-flow paths has a portion with an internal diameter that is less than each of the inlet inner diameter and the outlet inner diameter;
   C) a cell screening device comprising
      (a) an interior volume; and
      (b) a porous element having a pore structure that prevents the passage of microcarriers therethrough;
      (C) a plurality of ports in fluid communication with the interior volume of the device, the ports allowing fluid to pass into and/or out of the device, the plurality of ports including at least one inlet port, and at least one outlet port;
      wherein the cell screening device is arranged to allow fluid comprising cells and microcarriers to pass through the at least one inlet port into the interior volume of the cell screening device, the cells passing through the porous element and through the outlet port and along an outlet conduit, the microcarriers being retained by the porous element.

2. The cell separation system of claim 1, wherein:
the at least two separate first fluid sub-flow paths of the cell separation device further comprise a plurality of conduits fluidly connected by one or more connectors, each connector having at least one internal diameter; and
the at least two separate second fluid sub-flow paths of the cell separation device further comprise a plurality of conduits fluidly connected by one or more connectors, each connector having at least one internal diameter.

3. The cell separation system of claim 2, wherein the inlet inner diameter equals the outlet inner diameter.

4. A method of separating cells from microcarriers comprising:
passing a fluid comprising cells attached to microcarriers into the inlet of the cell separation device of the cell separation system of claim 2;
passing a first portion of the fluid and a second portion of the fluid through the cell shear device, including (a) passing the first portion of the fluid along the first flow path such that separate sub-portions of the first portion of the fluid pass along at the least two separate first fluid sub-flow paths wherein cells are detached from microcarriers; and (b) passing the second portion of the fluid along the second flow path such that separate sub-portions of the first portion of the fluid pass along at the least two separate first fluid sub-flow paths wherein cells are detached from microcarriers; and
passing detached cells and microcarriers through the outlet of the cell separation device.

5. The cell separation system of claim 1, wherein the inlet inner diameter of the cell separation device equals the outlet inner diameter.

6. The method of claim 4, further comprising passing detached cells and microcarriers into a cell settling device having a plurality of ports positioned at various heights on the front of the cell settling device, and passing detached cells and some microcarriers from one of the plurality of ports positioned at the front of the cell settling device into the cell screening device including a porous element therein, such that detached cells pass through the porous element and through an outlet port of the cell screening device, and microcarriers are retained by the porous element.

7. The method of claim 6, further comprising passing cells from the outlet port of the cell screening device into a harvest container.

8. The cell separation system of claim 1, further comprising D) a cell settling device.

\* \* \* \* \*